(12) United States Patent
Schoenen et al.

(10) Patent No.: US 6,251,935 B1
(45) Date of Patent: Jun. 26, 2001

(54) TREATMENT OF MIGRAINE BY ADMINISTRATION OF α-LIPOIC ACID OR DERIVATIVES THEREOF

(75) Inventors: Jean Schoenen, Beaufays-Chaudfontaine (BE); Jürgen Engel, Alzenau (DE); Klaus Wessel, Bad Vilbel (DE); Manfred Peukert, Warstein (DE); Michael Lobisch, Reichelsheim/Blofeld (DE); Harald Borbe, Mainz (DE)

(73) Assignee: ASTA Medica Aktiengesellschaft, Dresden (DE)

( * ) Notice: Subject to any disclaimer, the term of this patent is extended or adjusted under 35 U.S.C. 154(b) by 0 days.

(21) Appl. No.: 09/638,034

(22) Filed: Aug. 15, 2000

(30) Foreign Application Priority Data

Aug. 30, 1999 (DE) .............................................. 199 41 217

(51) Int. Cl.$^7$ .................................................... A61K 31/385
(52) U.S. Cl. ............................................................ 514/440
(58) Field of Search ............................................... 514/440

(56) References Cited

U.S. PATENT DOCUMENTS

| 5,118,505 | * | 6/1992 | Koltringer | .......................... 424/195.1 |
| 5,569,670 | * | 10/1996 | Weischer et al. | .................... 514/440 |
| 5,728,735 | * | 3/1998 | Ulrich et al. | .......................... 514/560 |

* cited by examiner

*Primary Examiner*—Raymond Henley, III
(74) *Attorney, Agent, or Firm*—Pillsbury Winthrop LLP

(57) ABSTRACT

The invention relates to the use of racemic α-lipoic acid or its enantiomers or pharmaceutically acceptable salts, amides, esters or thioesters thereof, in reduced or oxidized form, as active ingredient in the prevention or the acute or chronic treatment of migraine.

11 Claims, No Drawings

TREATMENT OF MIGRAINE BY ADMINISTRATION OF α-LIPOIC ACID OR DERIVATIVES THEREOF

This application claims priority from German Application No. 199 41 217.0, filed on Aug. 30, 1999, the subject matter of which is hereby incorporated herein by reference.

BACKGROUND OF THE INVENTION

1. Field of the Invention

The invention relates to the use of racemic α-lipoic acid or its enantiomers or pharmaceutically acceptable salts, amides, esters or thioesters thereof, in reduced or oxidized form, as active ingredient in the prevention of the acute or chronic treatment of migraine.

2. Background Information

Migraine is one of the most commonly occurring disorders. Migraine is defined by the International Headache Society (IHS) as a disorder characterized by episodic attacks of headache combined with autonomic symptoms. The painful episodes occur acutely and episodically, but the disorder itself must be regarded as chronic. In some patients without the so-called aura, the attacks of pain last for about 4 to 72 hours, are often unilateral and are associated with nausea and vomiting, and photo- and phonophobia. In patients with the so-called aura, reversible neurological signs such as aphasia, paresis, ataxia and dizziness occur a few minutes before an attack of pain. Epidemiological studies have shown that about 8 to 15% of the population suffer occasionally or frequently from mild to severe episodes of migraine. Women are usually affected more than men. Migraine normally appears for the first time at an age of 20 to 35, and is less common in children than in adults. The diagnosis is made by the physician only on the basis of the history and clinical data. There are no technical or biochemical methods providing a reliable diagnosis.

The pathophysiology and pathobiochemistry of migraine is underdeveloped. In the past, migraine has been regarded as a psychosomatic disorder without biological substrate, and it was unclear whether migraine is a physical disorder or a psychological health impairment. However, most experts no longer regard this as in doubt. It must, however, always be taken into account that psychological changes may induce migraine, and many other diverse factors such as hormonal (menstruation), nutritional (alcohol and malnutrition), medical (pharmaceuticals), environmental (noise) and psychological (stress) contribute to migraine. Patients still seek semi-professional assistance such as homeopathy or cell therapy.

In some patients, a reduction in the cerebral blood flow in isolated regions of the brain was associated with episodes of migraine (Lauritzen & Hansen, 1988). Perivascular changes stimulating afferent pain-conducting nerve fibres have been regarded, at least in some patients, as contributing to migraine (Moskowitz A. M. et al., Rev Neurol 145: 181–195; 1989), as have changes in various neurotransmitters (noradrenaline, serotonin, tachykinins etc.) (Edvinsson L. et al., in: Olesen J. Edvinsson L (ed.) Basic mechanisms of headache. Elsevier Science Publishers, Amsterdam 129–144; 1988). A reduction in the mitochondrial phosphorylation potential in the brain of migraine patients has been discussed recently, but it is still unclear whether this observation indicates primary deficits or represents only a secondary event in the pathophysiology of migraine (Schoenen et al., Neurology 50: 466–470; 1998).

Migraine is still treated only symptomatically. Some medications are used to modulate (β blockers) the so-called trigger factors for the episodes of migraine. Other compounds have vasoactivity (serotonin antagonists such as sumatriptan, non-steroidal anti-inflammatory drugs such as acetylsalicylic acid, anticonvulsants such as valproic acid). The vasoactivity of ergotamine does not, however, contribute to its clinical effects. Vitamin B2 is an important cofactor in the mitochondrial respiratory chain and, according to reports, reduces the occurrence of episodes of migraine in 68% of patients (Schoenen J. et al., loc. cit.). However, no vitamin $B_2$ deficiency has been observed in migraine patients, nor do patients with a vitamin $B_2$ deficiency show a clinical picture comparable with migraine.

All these possible interventions are pragmatic approaches to alleviating the symptoms of acute episodes of migraine at least in some patients. Various combinations of pharmaceuticals and other treatments are used in individual cases to achieve a clinical benefit. Pharmaceuticals are used either acutely to alleviate an episode of migraine or chronically to reduce the frequency of the episodes. Elimination of medical or environmental trigger factors is likewise an important attempt to help the patient. However, there is still no treatment of the underlying disease of migraine itself, which can be explained by lack of understanding of the pathophysiology of migraine. The benefit of pragmatic therapies is valuable for many suffering patients, but they still cannot be cured of their disorder.

α-Lipoic acid is a naturally occurring antioxidant and a cofactor of the glucose-metabolizing pyruvate dehydrogenase (Packer L. et al., Free Radicals in Biology & Medicine 19(2): 227–250, 1995) and is widely used for treating diabetic polyneuropathy (Ziegler D. et al., Diabetologia 38: 1425–1433; 1995). In addition, α-lipoic acid has been used for decades for treating liver disorders (Bode J. Ch. et al., DMW 112 (9), 349–352; 1987) and poisoning by fungi (Brunn J. et al., Internist. Prax. 19: 475–478, 1979). The molecular mode of action has recently been characterized as that of the diabetes-specific antioxidant (Nagamatsu M. et al., Diabetes Care 18 (8): 1160–1167; 1995).

The biological and therapeutic effects of α-lipoic acid in oxidized and reduced form are also found with numerous derivatives as metabolites, sometimes in diminished and sometimes in improved form (for example 3-ketolipoic acid, 1,2-diselenolane-3-pentanoic acid, lipoamide, octotiamine, 2-(N,N-dimethylamine)ethylamidolipoate HCl, tocopheryl lipoate and tocotrienyl lipoate, gamma-hydroxybutyrat lipoate, lipoic acid vitamin E ester, N-acetyl-p-aminophenol derivatives of lipoic acid and others (Tirosh O. Sen CK, Roy S, Kobayashi S, Packer L. Neuroprotective effects of α-lipoic acid and ist positively charged amide analogue. Free Rad Biol Med 26 (11/12), 1418–1426, 1999); EP 0 855 396 A1, EP 0 869 126 A1, PCT/GB98/02155, WO 99/06040, DE 43 27 462 A1). These derivatives were proposed in order to improve the metabolism and the distribution in vivo, which may also apply to the distribution into the central nervous system. Some derivatives may also improve the effects (for example affinity and turnover rate) on the biological targets (biological redox systems such as α-ketoacid dehydrogenases, H protein, thioredoxin, glutathione reductase or cellular redox systems such as glutathione, ubiquinone, complex I of the respiratory chain, or redox- and SH-sensitive proteins and enzymes, the NO system, catalase, the cellular cystine/cysteine shuttle, homocysteine, tyrosine kinase, MAP kinase, metal ions (for complexation), alpha-1-antiproteinase, or redox-sensitive transcription factors such as NF-kB or AP1) of α-lipoic acid, or couple other active molecules with α-lipoic acid with the aim of a synergistic or additive pharmacological effect.

The term "α-lipoic acid" is therefore used in this text as a general term which, apart from the enantiomers, the racemate and mixtures of the enantiomers, also covers derivatives (esters, thioesters, ethers, salts, amides, metabolites etc.) as long as the active dithiolane group of the α-lipoic acid continues to be partly responsible for the biological and medical effect of the derivative.

Pharmaceuticals with α-lipoic acid have been obtainable for decades and are well tolerated. In this time, many possible uses have been tested, but a benefit in the treatment of migraine has never been reported.

SUMMARY OF THE INVENTION

The aim of the invention is to improve the state of health of migraine patients.

This object is achieved by the use of racemic α-lipoic acid or its enantiomers or pharmaceutically acceptable salts, amides, esters or thioesters thereof, in reduced or oxidized form, as active ingredient for the prevention or the acute or chronic treatment of migraine.

The benefit derives from a reduction in the severity and, even more important, the frequency of episodes of migraine. In the most favourable case, chronic use of α-lipoic acid or its abovementioned derivatives makes it possible completely to cure the migraine through the disappearance of all episodes.

Another important advantage of the invention is that the active ingredients used are very well tolerated.

The active ingredient can be formulated in a pharmaceutical for oral or parenteral administration, or be administered in the form of a food supplement or medical food for parenteral nutrition.

Suitable preparations are known from the patent literature and are described, for example, in the following publications:
EP 0858 802 A2
EP 0318 891 A1
EP 0 560 092 B1
U.S. Pat. No. 5,650,429 A
U.S. Pat. No. 5,334,612 A
U.S. Pat. No. 5,569,670 A The products manufactured in this way can be placed on the market labelled for the purpose of use, it being necessary to comply with the appropriate national regulations for the instructions for use for professionals and the patient. The products may in this case normally be subject to the legal framework for pharmaceuticals or, where appropriate, also food supplements.

The dosage of active ingredient is normally in the range from 100 to 1800, preferably 200 to 1200, in particular 200 to 600, mg of racemic α-lipoic acid per day or, based on the dithiolane residue, an equivalent dose of one of the other active ingredients, this total dose being administered once a day or divided into two or three daily doses.

Derivatives of α-lipoic acid in reduced or oxidized form (for example salts, esters, thioesters, ethers, amides, metabolites) can be employed analogously as long as they are administered in a dose that equivalent concentrations or biological effects on the target structures (biological redox systems) are achieved.

Preference is given to the use of dextrorotatory α-lipoic acid (R(+)-α-lipoic acid or R(−)-dihydrolipoic acid) or derivatives.

A further preferred embodiment of the invention consists in the administration of the active ingredient in free of fixed combination with another substance, or several, used for treating migraine.

Preferred examples of combination partners are sumatriptan or another compound from the triptan group, ergotamine or a derivative thereof, a β blocker, an anticonvulsant, an analgesic, an anti-emetic or a calcium channel blocker, without the invention being limited to these.

It is likewise advantageous to administer the active ingredient as free or fixed combination with vitamins, antioxidants and/or biologically functional cofactors. Vitamin $B_2$ is particularly preferred in this connection.

The invention is explained below by means of examples without being limited to these.

DETAILED DESCRIPTION OF THE INVENTION

PHARMACEUTICAL EXAMPLES

Example 1

Tablets with 600 mg of racemic α-lipoic acid 1200 g of racemic α-lipoic acid with a particle size of 60%>100 μm are mixed with 120 g of low-substituted hydroxypropylcellulose (L-HPC-LH 22/Shin Etsu), and the mixture is moistened and kneaded with 600 g of purified water.

After passing through a sieve with a mesh width of 2 mm the granules are dried, again sieved through a sieve with a mesh width of 1 mm and, after admixing 48 g of magnesium stearate, compressed to tablets in oblong form and with a weight of 684 g, a length of 18 mm, a width of 8 mm and a radius of curvature of 6 mm. One tablet contains 600 mg of racemic α-lipoic acid.

The tablets can subsequently be provided by conventional standard methods with a film coating which is soluble in gastric fluid or permeable to gastric fluid.

Example 2

Ampoules with 200 mg of racemic α-lipoic acid as trometamol salt in 10 ml were added to 250 g of racemic α-lipoic acid and dissolved with stirring together with 352.3 g of trometamol (2-amino-2-(hydroxymethyl)-1,3-propanediol) in a mixture of 9 litres of water for injections and 200 g of 1,2-propylene glycol. The solution is made up to 12.5 litres with water for injections and then filtered through a membrane filter with a pore width of 0.2 μm with a glass fibre prefilter. The filtrate is dispensed in 10 ml portions under aseptic conditions into sterilized 10 ml ampoules. One ampoule contains 200 mg of racemic α-lipoic acid as trometamol salt in 10 ml of solution for injection.

Clinical Examples

Racemic α-lipoic acid was administered to migraine patients orally in a daily dose of 200–600 mg acutely and chronically in the form of commercially available dosage forms of various strengths. The active ingredient was administered either as a single dose in the morning or as required during the day. The frequency and severity of episodes of migraine were compared with the period before the treatment. The active ingredient was administered to patients who were either untreated or who were already receiving therapy and had previously been treated with other anti-migraine active ingredients and had not responded well to their previous treatment.

|   | Patient Treatment | Clinical effect |
|---|---|---|
| 1 | No previous treatment | 50% reduction in the frequency of migraine attacks |
| 2 | Previous treatment with valproate, then replaced by α-lipoic acid | Effect of the treatment with valproate maintained after the replacement |
| 3 | Previous treatment with vitamin $B_2$ | 100% reduction in the frequency of migraine attacks |
| 4 | Previous treatment with vitamin $B_2$ | 100% reduction in the frequency of migraine attacks |
| 5 | Previous treatment with valproate | 50% reduction in the frequency of migraine attacks |
| 6 | Previous treatment with valproate, vitamin $B_2$ and acetylsalicylic acid | 80% reduction in the frequency of migraine attacks |
| 7 | Previous treatment with valproate | 50% reduction in the frequency of migraine attacks |
| 8 | Previous treatment with valproate | 50% reduction in the severity of migraine attacks |
| 9 | No previous treatment | 75% reduction in the frequency of migraine attacks |
| 10 | Previous treatment with cyclandelate | 40% reduction in the frequency of migraine attacks |
| 11 | No previous treatment | 30–100% reduction in the severity of attacks on the day after taking 200–600 mg of α-lipoic acid |

For assessment of these observations in the medical treatment of migraine patients, it must be taken into account that the extent of the effects found, measured by the experience with other therapies, is very remarkable. In particular, the effect in otherwise therapy-resistant patients must be designated noteworthy and surprising. This underlines the value of the invention for the future treatment of migraine.

What is claimed is:

1. A method for the prevention or treatment of migraine comprising the administration of an active ingredient selected from the group consisting of racemic α-lipoic acid, enantiomers and pharmaceutically acceptable salts, amides, esters or thioesters thereof, in reduced or oxidized form, to an individual in need thereof.

2. The method according to claim 1, wherein the severity or frequency of migraine attacks is reduced.

3. The method of claim 1, wherein the active ingredient is in the form of a pharmaceutical.

4. The method of claim claim 1, wherein the active ingredient is in the form of a food or food supplement for parenteral nutrition.

5. The method according to claim 1, wherein the active ingredient is administered in a dosage of 100 to 1800 mg of racemic α-lipoic acid per day or, based on the dithiolane residue, an equivalent dose of one of the other active ingredients.

6. The method according to claim 1, wherein the active ingredient is administered in a dosage of 200 to 1200 mg of racemic α-lipoic acid per day or, based on the dithiolane residue, an equivalent dose of one of the other active ingredients.

7. The method according to claim 1, wherein the active ingredient is administered in a dosage of 200 to 600 mg of racemic α-lipoic acid per day or, based on the dithiolane residue, an equivalent dose of one of the other active ingredients.

8. The method according to one of claims 5–7, wherein the dosage is administered once a day or divided into two or three daily doses.

9. The method according to claim 1, wherein the active ingredient is administered in free or fixed combination with at least one other substance used for treatment of migraine.

10. The method according to claim 9, wherein the other substance is selected from the group consisting of sumatriptan and other compounds from the triptan group, ergotamine and derivatives thereof, β-blockers, anticonvulsants, analgesics, antiemetics and calcium channel blockers.

11. The method according to claim 1, wherein the active ingredient is administered in free or fixed combination with vitamins, antioxidants and/or biologically functional cofactors.

* * * * *